United States Patent
Hara et al.

(10) Patent No.: US 8,031,928 B2
(45) Date of Patent: Oct. 4, 2011

(54) CT DATA PROCESSING APPARATUS AND CT DATA PROCESSING METHOD

(75) Inventors: Yukihiro Hara, Hino (JP); Ayuta Yamada, Ome (JP); Yuichi Kodama, Hachioji (JP)

(73) Assignee: Rigaku Corporation, Tokyo (JP)

( * ) Notice: Subject to any disclaimer, the term of this patent is extended or adjusted under 35 U.S.C. 154(b) by 1027 days.

(21) Appl. No.: 11/907,360

(22) Filed: Oct. 11, 2007

(65) Prior Publication Data

US 2008/0130975 A1 Jun. 5, 2008

(30) Foreign Application Priority Data

Oct. 13, 2006 (JP) .................................. 2006-280555

(51) Int. Cl.
*G06K 9/00* (2006.01)
(52) U.S. Cl. ............................ 382/131; 378/53; 378/901
(58) Field of Classification Search .................. 378/53, 378/901; 382/131
See application file for complete search history.

(56) References Cited

U.S. PATENT DOCUMENTS

| | | | | |
|---|---|---|---|---|
| 6,198,797 | B1 * | 3/2001 | Majima et al. ................... | 378/98 |
| 7,103,139 | B2 * | 9/2006 | Nagaoka et al. ................. | 378/16 |
| 7,949,171 | B2 * | 5/2011 | Qing et al. ...................... | 382/131 |

FOREIGN PATENT DOCUMENTS

JP 2003-339694 A 12/2003

OTHER PUBLICATIONS

Radiology vol. 211, No. 1, pp. 283-286 (Apr. 1999), (The Radiological Society of North America) pp. 283-286.

* cited by examiner

*Primary Examiner* — Allen C. Ho
(74) *Attorney, Agent, or Firm* — Birch, Stewart, Kolasch & Birch, LLP

(57) ABSTRACT

A CT data processing apparatus and a CT data processing method capable of separating a subcutaneous fat region from a visceral fat region accurately and efficiently in CT data are provided. The CT data processing apparatus includes a center calculation part that calculates a body center 41 of an examinee on tomographic CT data, a start point setting part that identifies a vertebral column position 45 on the tomographic CT data and sets a start point on a muscular layer 37 on the opposite side of the vertebral column position 45 with respect to the body center 41, a muscular layer determination part that determines whether or not the muscular layer 37 is present in a first range 48, and when it is determined that the muscular layer 37 is present in the first range 48, further setting a point on the muscular layer 37 in the first range 48 as a new first reference point 47 and thus determining whether or not the muscular layer 37 is present in the first range 48, while moving the first reference point 47 from the start point 46, and a separation line calculation part that calculates a separation line so that the separation line passes through the first reference points 47.

12 Claims, 9 Drawing Sheets

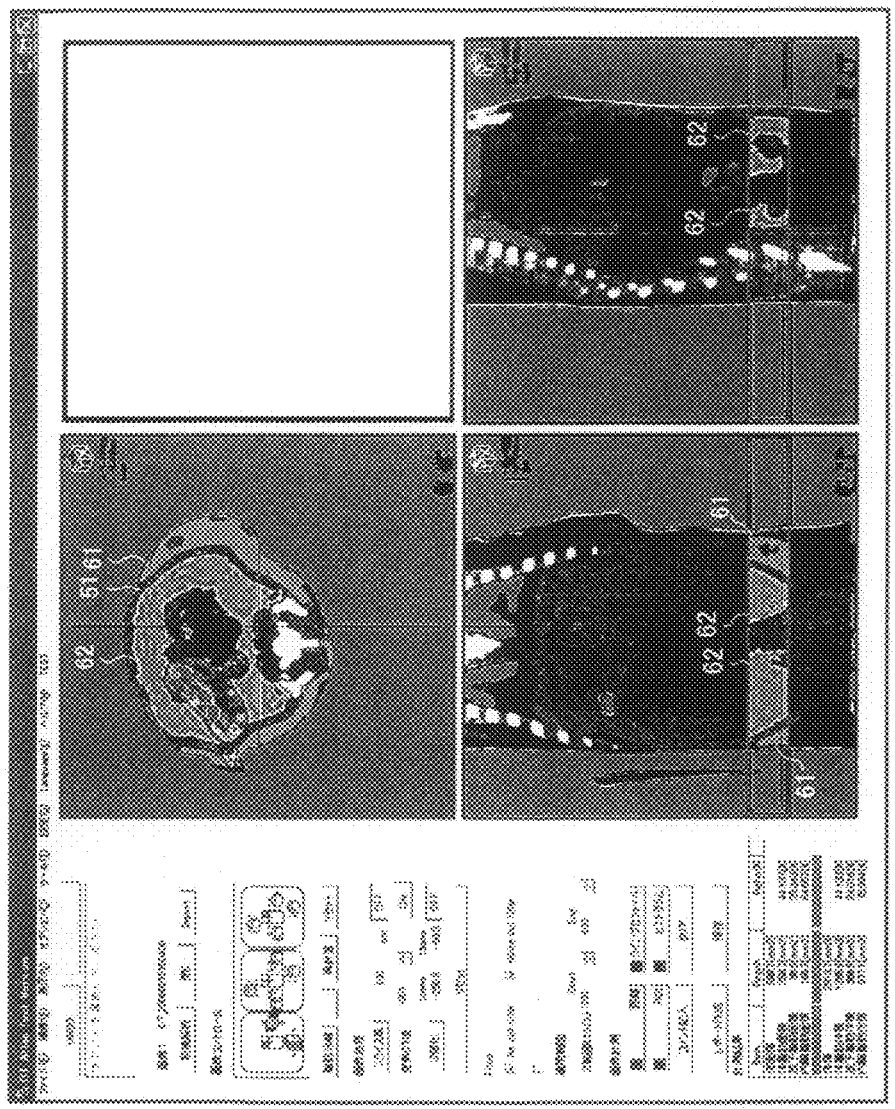

CT DATA PROCESSING APPARATUS AND CT DATA PROCESSING METHOD

BACKGROUND OF THE INVENTION

1. Field of the Invention

The present invention relates to a CT data processing apparatus and a CT data processing method for separating a region indicative of subcutaneous fat from a region indicative of visceral fat on CT (Computer Tomography) data of an examinee.

2. Description of the Related Art

Conventionally, a technique is known, in which tomographic data of a small animal is imaged by X-ray CT tomography and the amount and position of fat are analyzed based on the tomographic data. Fat includes subcutaneous fat and visceral fat and there is sometimes a case where they need to be distinguished from each other for evaluation. However, the CT values of both the fats are −250 to −50 and therefore it is not possible to distinguish between the respective fat regions using the CT values.

In order to deal with this problem, various methods of separating fat regions have been developed. Among them, there is a method in which a person who measures draws a separation line based on his/her impression of a CT image. Since it requires the person who measures to draw a separation line, many man-hours and much time are necessary and not efficient, although an exact separation line can be drawn. On the other hand, a method is known, in which a separation line is drawn automatically by processing (for example, refer to Japanese Unexamined Patent Publication No. 2003-339694).

In the tomographic image processing apparatus stated in Japanese Unexamined Patent Publication No. 2003-339694, the muscular layer between subcutaneous fat and visceral fat is focused on and then the skin layer is removed by image processing, the region of muscular layer is extended to separate between the respective fats and the subcutaneous fat is extended inwardly by the amount of the extended muscular layer.

However, in such an image processing apparatus as described above, the fat region itself to be evaluated is removed or extended. Although its effect is canceled out by extending the fat region afterward by the amount of removed region, however, there is the possibility that the result to be obtained may be incorrect because the fat region deforms into one different from the original one. In addition, if separation is not accurate, it will be required to modify the separation, and after all, the working efficiency is decreased.

SUMMARY OF THE INVENTION

The present invention has been developed in view of such circumstances and an object thereof is to provide a CT data processing apparatus and a CT data processing method capable of separating the subcutaneous fat region from the visceral fat region accurately and efficiently on CT data.

(1) In order to achieve the above-mentioned object, a CT data processing apparatus according to the present invention comprises a center calculation part that identifies a body surface region of an examinee on tomographic CT data and calculates a body center from the shape of the body surface, a start point setting part that identifies vertebral column position on the tomographic CT data and sets a start point at which a first reference point for determination is initially placed on the muscular layer on the opposite side of the vertebral column position with respect to the body center, a muscular layer determination part that determines whether or not a muscular layer is present in a first range set based on the first reference point and when it is determined that the muscular layer is present in the first range, setting a point on the muscular layer in the first range as the new first reference point and thus determining whether or not the muscular layer is present in the first range while moving the first reference point from the start point, and a separation line calculation part that calculates a separation line so that the separation line that separates the subcutaneous fat region from the visceral fat region passes through the first reference points.

As described above, since the separation line is calculated by determining whether or not the muscular layer is present based on the body center of the examinee, it is possible to separate the fat region accurately and efficiently by a method that resembles the method of drawing a separation line by visual recognition by a person. In addition, since the separation line is calculated by searching for the muscular layer in the range set based on the reference point, it is possible to calculate an accurate separation line.

(2) In the CT data processing apparatus according to the present invention, the muscular layer determination part sets the first range in a region advanced from the first reference point in the arc direction of circle or ellipse with the body center as center and determines whether or not the muscular layer is present.

As described above, since the muscular layer determination part sets the first range at the position advanced from the first reference point in the arc direction of circle or ellipse, it is possible to find the muscular layer and calculate the separation line efficiently.

(3) In the CT data processing apparatus according to the present invention, the separation line calculation part calculates a separation line by linking the traces of the first reference points by arcs of circle or ellipse with the body center as center.

Due to this, it is possible to calculate a separation line naturally continuous on the whole. In some cases, the muscular layer may not be continuous along the circumference and partly discontinuous on the tomographic CT data. Even in such a case where the muscular layer is not continuous, it is also possible to calculate a natural separation line by connecting the points on the muscular layer by arcs of circle or ellipse with the body center as center.

(4) In the CT data processing apparatus according to the present invention, there is further provided a determination condition setting part that sets a condition for determination that a muscular layer is not present in a body surface region in order to distinguish the body surface region from the muscular layer both having the equivalent CT value prior to the determination.

Due to this, even if there is a portion where it is not possible to distinguish the muscular layer from the body surface region using the CT value because they are in contact with each other, the separation line is not determined to be on the body surface region. As a result, it is possible to calculate the separation line accurately.

(5) The CT data processing apparatus according to the present invention comprises a muscular layer determination part determining whether or not a muscular layer is present in a second range set based on a second reference point, in tomographic CT data next to tomographic CT data for which a separation line separating a subcutaneous fat region from a visceral fat region of an examinee has already been calculated, while moving the second reference point for determination on a tomographic path identical to the calculated separation line; and a separation line calculation part calculating a separation line so that the separation line passes through a point on the muscular layer in the second range when it is determined that the muscular layer is present in the second range.

Since the muscular layer is continuous, the separation line of the tomographic CT data to be calculated does not differ very much from the separation line of the neighboring tomographic CT data. In the CT data processing apparatus according to the present invention, the separation line is calculated in the neighboring tomographic CT data using the separation line of the tomographic CT data already calculated, and therefore, it is possible to calculate the separation line accurately and efficiently.

(6) In the CT data processing apparatus according to the present invention, the separation line calculation part separates the subcutaneous fat region from the visceral fat region three-dimensionally by repeating calculation of a separation line in each of the second and subsequent tomographic CT data.

As described above, in the CT data processing apparatus according to the present invention, the calculation of the separation line in the neighboring tomographic CT data is repeated using the separation line in the tomographic CT data already calculated, and therefore, it is possible to separate each fat region efficiently using the three-dimensional CT data.

(7) A CT data processing method according to the present invention causes a computer to execute center calculation processing for calculating a body center of an examinee on tomographic CT data; start point setting processing for identifying a vertebral column position on the tomographic CT data and setting a start point at which a first reference point for determination is initially placed on a muscular layer on the opposite side of the vertebral column position with respect to the body center; a muscular layer determination processing for determining whether or not a muscular layer is present in a first range set based on the first reference point, and when it is determined that the muscular layer is present in the first range, setting a point on the muscular layer in the first range as a new first reference point and thus determining whether or not the muscular layer is present in the first range while moving the first reference point from the start point; and a separation line calculation processing for calculating a separation line so that the separation line separating a subcutaneous fat region from a visceral fat region passes through the first reference points.

As described above, since the separation line is calculated by determining whether or not the muscular layer is present based on the body center of the examinee, it is possible to separate the fat region accurately and efficiently by a method that resembles the method of drawing a separation line by visual recognition by a person. In addition, since the separation line is calculated by searching for the muscular layer in the range set based on the reference point, it is possible to calculate an accurate separation line.

(8) The CT data processing method according to the present invention causes a computer to execute a muscular layer determination processing for determining whether or not a muscular layer is present in a second range set based on a second reference point, in tomographic CT data next to tomographic CT data for which a separation line separating a subcutaneous fat region from a visceral fat region of an examinee has already been calculated, while moving the second reference point for determination on a tomographic path identical to the calculated separation line; and a separation line calculation processing for calculating a separation line so that the separation line passes through a point on the muscular layer in the second range when it is determined that the muscular layer is present in the second range.

Since the muscular layer is continuous, the separation line of the tomographic CT data to be calculated does not differ very much from the separation line of the neighboring tomographic CT data. In the CT data processing method according to the present invention, the separation line is calculated in the neighboring tomographic CT data using the separation line of the tomographic CT data already calculated, and therefore, it is possible to calculate the separation line accurately and efficiently. As a result, it is possible to separate each fat region using the three-dimensional CT data with almost no modification.

According to the present invention, since the separation line is calculated by determining whether or not the muscular layer is present based on the body center of the examinee, it is possible to separate the fat region accurately and efficiently by a method that resembles the method of drawing a separation line by visual recognition by a person. In addition, since the separation line is calculated by searching for the muscular layer in the range set based on the reference point, it is possible to calculate an accurate separation line.

BRIEF DESCRIPTION OF THE DRAWINGS

FIG. 9 is an image showing the result of separation processing of fat region.

DETAILED DESCRIPTION OF THE INVENTION

Figure 1:
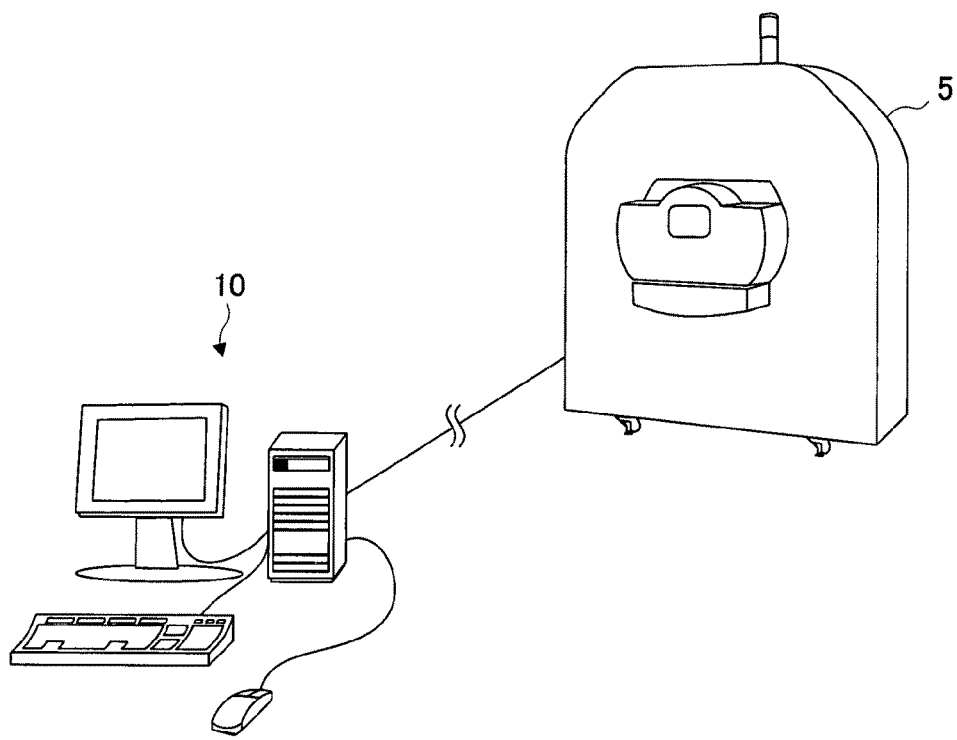
FIG. 1 is a conceptual diagram showing a configuration of an X-ray CT apparatus and a CT data processing apparatus.

Best Modes for Carrying Out the Invention

Embodiments of the present invention will be described below with reference to drawings. In order to facilitate understanding of the description, the same reference numerals are assigned to the same components in each drawing and duplicated description is omitted.

(Configuration of Apparatus)

FIG. 1 is a conceptual diagram showing a configuration of an X-ray CT apparatus 5 and a CT data processing apparatus 10. The X-ray CT apparatus 5 has a micro focus X-ray source in which the focus size of an X-ray is in units of micron and a two-dimensional X-ray detector and converts X-rays received by a plane into electric signals to obtain an image. In detection, the pixel size of tomographic data can be set between, for example, 20 μm and 135 μm. The X-ray source and the detector are attached to a rotary arm, which rotates 360 degrees about a predetermined rotation axis. The X-ray CT apparatus 5 has a support base to place an examinee, such as rat, mouse, etc., and the support base is slid and put into the X-ray CT apparatus 5 thorough a gantry hole.

Figure 2:
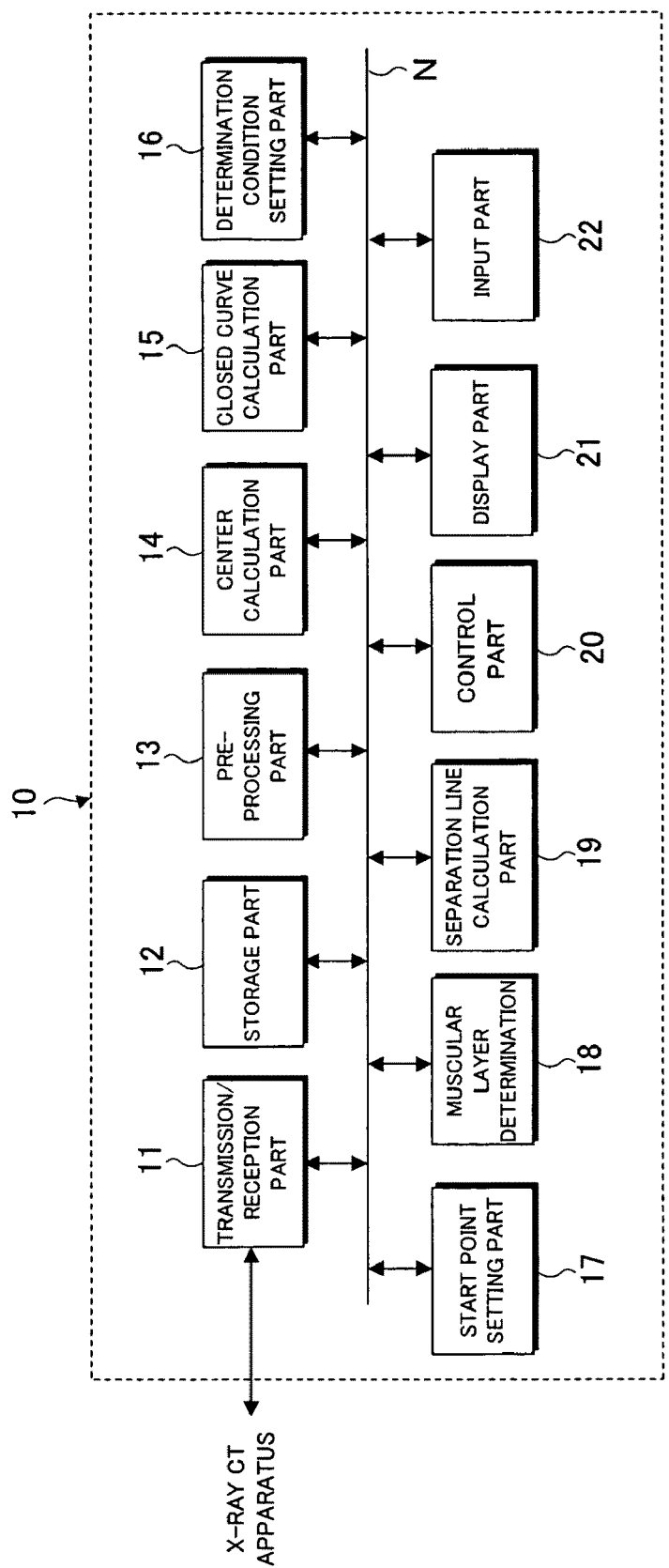
FIG. 2 is a block diagram showing a functional configuration of a CT data processing apparatus according to the present invention.
Figure 3:
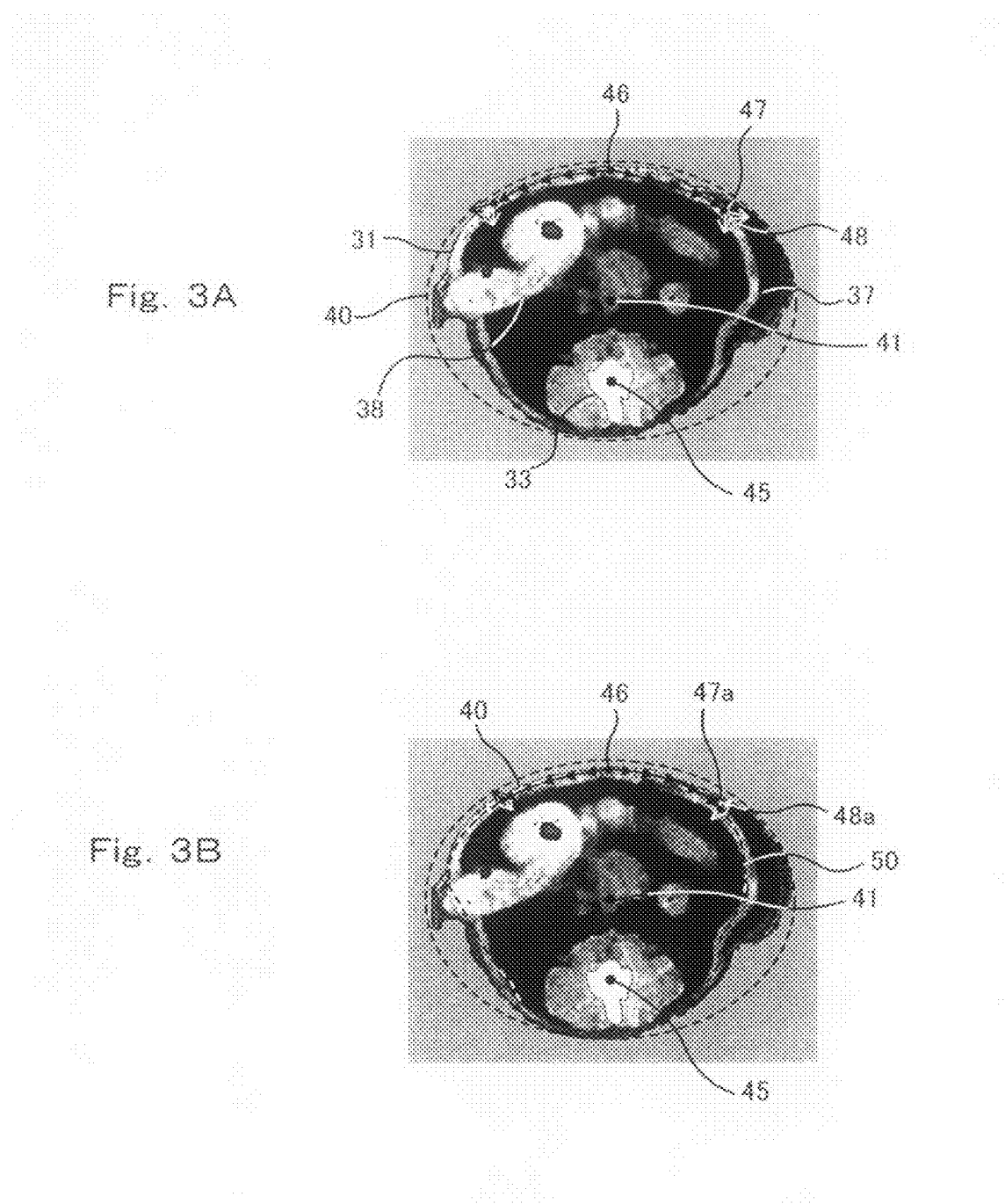
FIG. 3A is a diagram showing first tomographic CT data having been imaged.
FIG. 3B is a diagram showing second and subsequent tomographic CT data having been imaged.

FIG. 2 is a block diagram showing a functional configuration of the CT data processing apparatus 10. The CT data processing apparatus 10 includes a transmission/reception part 11, a storage part 12, a pre-processing part 13, a center calculation part 14, a closed curve calculation part 15, a determination condition setting part 16, a start point setting part 17, a muscular layer determination part 18, a separation line calculation part 19, a control part 20, a display part 21, an input part 22, and a control bus N. The control bus N is a trunk line shown conceptually, which is used for transmission/reception of signals and data between respective parts. FIG. 3A is a diagram showing first tomographic CT data having been imaged and FIG. 3B is a diagram showing second and later tomographic CT data having been imaged. The solid triangular arrow in FIGS. 3A and 3B indicates the direction of movement of a reference point 47 so far and the V-shaped arrow indicates a range 48 at present. This also applies to the subsequent drawings. The function of each part will be described using these drawings. Incidentally, in FIGS. 3A and 3B, the air region is shown by a bright color for convenience.

The transmission/reception part 11 is an interface and transmits and receives signals to and from the X-ray CT apparatus 5 and receives data from the X-ray CT apparatus 5. The storage part 12 is constituted by a memory or an external storage device such as a hard disk etc. and stores data and programs.

The pre-processing part 13 is constituted by a CPU and carries out the processing necessary in advance for determination processing. For example, the pre-processing part 13 reads tomographic CT data from the storage part 12 and carries out processing of changing data at a portion in contact with air to the CT value of air or processing of changing data in the region of the support base to the CT value of air.

The center calculation part 14 identifies a body surface region 31 of an examinee on the tomographic CT data as shown in FIG. 3A and calculates s body center 41 from the shape of the body surface. The body surface region 31 has a CT value of 50 to 100 and identified by the CT value. In other words, the region is in contact with air or the region after the support base processing and is capable of identifying the body surface region 31 by identifying the region having the CT value of the body surface organ. Then, the maximum value and the minimum value are calculated in the body surface region 31 as to components of two axes perpendicular to each other and a point at the middle value between the maximum value and the minimum value is extracted for each axis. This point can be regarded as the body center 41 and when the contour of the body is grasped as an ellipse, this will be the center of the ellipse. The center calculation part 14 is constituted by a CPU. In the above-mentioned method, the center of the ellipse in contact with the body surface is sought for by regarding it as the body center 41, however, there may be methods of seeking for the body center 41 other than that described above.

The closed curve calculation part 15 calculates a closed curve 43 in contact with the body surface based on the body center 41. For example, as shown in FIG. 3A, the closed curve calculation part 15 calculates a circle with the body center 41 as center as a closed curve. In such a case, a circle in contact with the body surface region 31 is sought for. The closed curve 43 may be an ellipse with the body center 41 as center. In such a case, for example, an ellipse in contact with the body surface region can be calculated by setting its minor axis in the direction toward the point closest to the body center in the body surface region and major axis in the direction perpendicular thereto. The closed curve 43 is used when setting a range in which the muscular layer 37 is determined. In particular, if a circle or ellipse is used as the closed curve 43, it is possible to draw a biologically natural separation line. The closed curve calculation part 15 is constituted by a CPU.

Before determination, the determination condition setting part 16 sets the condition so that it is determined that the muscular layer 37 is not present in the body surface region. The muscular layer and the body surface region have almost the same CT value and it is not possible to distinguish between them using the CT value. For example, the determination condition setting part 16 sets so that the CT value of the body surface region is changed to the CT value of air only during the period of determination processing. Due to this, even if there exists a portion in which the muscular layer 37 is in contact with the body surface region 31 and their regions cannot be distinguished using the CT value, it is not determined that a separation line is present in the body surface region 31. As a result, a separation line can be calculated accurately. The determination condition setting part 16 is constituted by a CPU.

The start point setting part 17 identifies a vertebral column position 45 using tomographic CT data. Then, the start point setting part 17 sets a start point 46 to determine whether or not the muscular layer 37 is present on the muscular layer 37 on the opposite side of the vertebral column position 45 with respect to the body center 41. The CT value of the vertebral column is about 1,000 and therefore it is possible to identify a vertebral column region 33 by the CT value. Then, the start point 46 is set on the opposite side with respect to the body center 41 with the center of the vertebral column region 33 as the vertebral column position 45. Due to this, it is possible to trace the muscular layer 37 with the vertebral column region 33 as target. By utilizing the vertebral column region 33 as target, it is possible to easily determine whether or not the determination as to presence or absence of the muscular layer 37 is completed. When setting a start point on the belly side, a point nearer to the center by a predetermined number of pixels from the boundary between the body surface region 31 and the air region is set as the start point. The start point 46 will be substantially a point on the muscular layer around the navel. The start point setting part 17 is constituted by a CPU. A setting means of a start point is not limited to that described above and any means that sets a start point on the muscular layer 37 on the belly side can be accepted.

The muscular layer determination part 18 determines whether or not a muscular layer is present in the range (first range) determined by the reference point 47 while moving the reference point 47 (first reference point) for determination both clockwise and counterclockwise from the start point 46 toward the vertebral column region 33. The reference point 47 (first reference point) is a reference point when determining whether or not the muscular layer is present. The range 48 (first range) includes a point advanced by a predetermined central angle θ with the body center 41 as center in the arc direction of a similar curve of the closed curve 43 from the reference point 47 and is a range that has its width in the radial direction from the body center 41. When the muscular layer determination part 18 determines that the muscular layer 37 is present in the range 48, the reference point 47 is moved in a constant direction by the predetermined central angle θ with the middle point of the muscular layer 37 in the range 48 as the new reference point 47.

As described above, it is possible to separate the fat region both accurately and efficiently by a method similar to one in which a person draws a separation line by visual recognition in order to determine the presence of the muscular layer 37 along the closed curve 43 based on the shape of the body surface. Even when the muscular layer 37 is not present on an arc of a similar curve of the closed curve 43, since a separation line is calculated by searching for the muscular layer 37 in the range 48 having its width in the radial direction from the body center 41, it is possible to calculate an accurate separation line. The muscular layer determination part 18 moves the reference point 47 on the closed curve in the constant direction by the predetermined central angle each time with the body center as centrer. Since the reference point 47 is moved by the predetermined central angle as described above, it is possible to calculate a separation line efficiently by setting the predetermined central angle properly. The preferable angle of the predetermined central angle is about 5 degrees. The central angle does not necessarily have to be constant as described above. The muscular layer determination part 18 determines whether or not the muscular layer 37 is present in the setting that the muscular layer 37 is not present in the body surface region 31 as described above.

In addition, the muscular layer determination part 18 determines whether or not the muscular layer 37 is in contact with a visceral 38 (parenchymatous organ). This determination is made based on the size of the range that has the CT value equivalent to that of the muscular layer 37. In other words, when it is determined that the muscular layer 37 is present, which is remarkably thicker than a general muscular layer, it is determined that the muscular layer 37 is in contact with the visceral 38. Further, when it is determined that the muscular layer 37 is in contact with the visceral 38, a point moved inwardly to the side of the muscular layer 37 from the side of the body surface region 31 by a few pixels is set as the reference point 47.

As shown in FIG. 3B, the muscular layer determination part 18 utilizes already processed data when analyzing three-dimensionally continuous tomographic data. In other words, the muscular layer determination part 18 moves a reference point 47a (second reference point) on a path 50 identical to that of the calculated separation line when processing the tomographic CT data next to the tomographic CT data the separation line of which has already been calculated. The direction of movement is both clockwise and counterclockwise. A range 48a (second range) is a range that has its width in the radial direction from the body center with the reference point 47a as center. Since the muscular layer 37 is continuous, the separation line of the tomographic CT data to be calculated does not differ very much from the separation line of the neighboring tomographic CT data. Since the separation line of the neighboring tomographic CT data is calculated using the already calculated separation line of the tomographic CT data, it is possible to calculate the separation line both accurately and efficiently. As a result, it is possible to separate each fat region with the three-dimensional CT data with almost no modification. Incidentally, the neighboring tomographic CT data is tomographic CT data continuous to the already processed tomographic CT data in the thickness direction of the tomogram. The muscular layer determination part 18 is constituted by a CPU.

In addition, the muscular layer determination part 18 determines whether or not the first tomographic data processing and the continuous tomographic data processing are completed by determining whether or not the vertebral column region 33 is in the range 48 or the range 48a. Whether or not the vertebral column region 33 is present is determined using the CT value.

The separation line calculation part 19 calculates a separation line that connects points on the muscular layer 37 when it is determined that the muscular layer 37 is in the range 48a. When it is determined that the muscular layer 37 is present, the central point of the muscular layer 37 is stored in the storage part 12 and a separation line that passes through the stored point is calculated later. The middle point of the muscular layer 37 is the middle point of a segment formed by overlap of the muscular layer 37 and a straight line connecting the body center and the reference point 47a. Then, the separation line calculation part 19 calculates a separation line by connecting the middle points on the muscular layer by arcs of a circle with the body center 41 as center. Due to this, it is possible to calculate a separation line naturally continuous on the whole. Even if the muscular layer 37 is not continuous along the circumference and partly discontinuous, it is also possible to calculate a natural separation line by connecting the points on the muscular layer 37 by arcs of circle or ellipse with the body center 41 as center.

The separation line calculation part 19 repeats the calculation of a separation line in the second and subsequent tomographic CT data when analyzing the CT data three-dimensionally. Then the separation line calculation part 19 separates the subcutaneous fat region from the visceral fat region in the three-dimensional CT data. The separation line calculation part 19 is constituted by a CPU.

The control part 20 is constituted by a CPU and controls each part. The display part 21 is, for example, an LCD monitor and displays CT data as tomogram or three-dimensional image, or displays CUI, GUI for operation. The input part 22 is constituted by a pointing device such as keyboard, mouse, etc., and used when a user inputs.

(Processing Operation)

Figure 4:
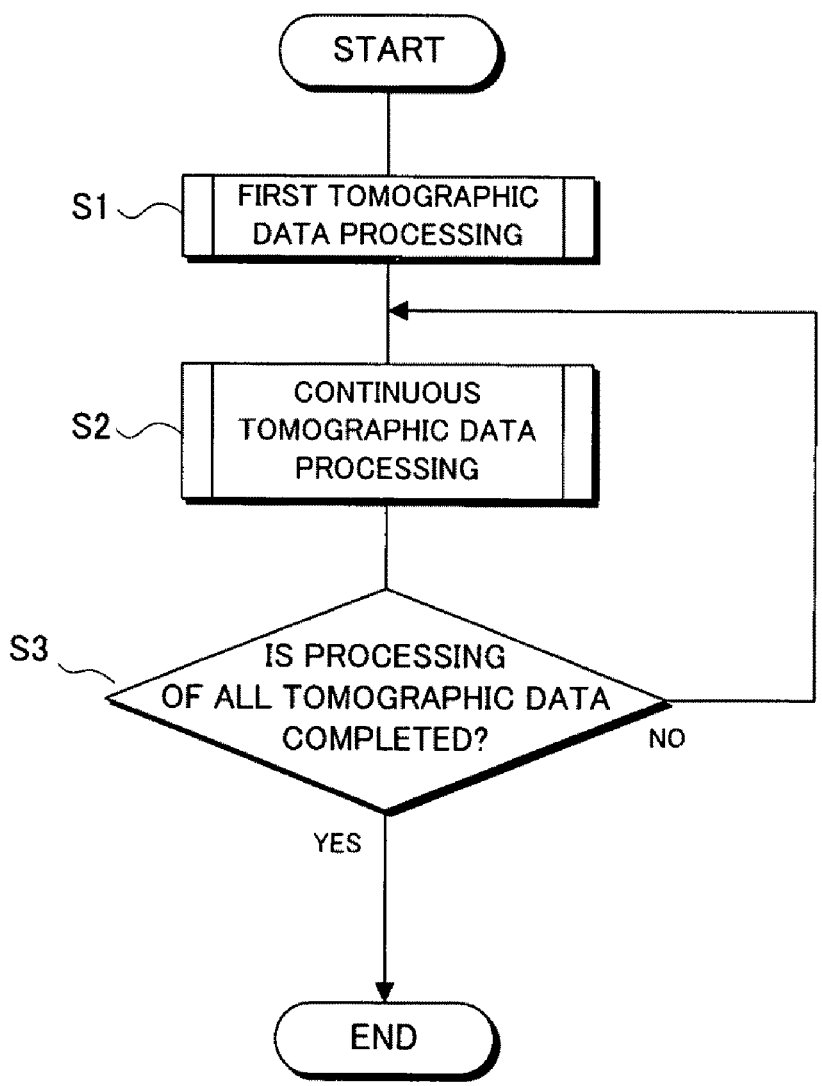
FIG. 4 is a flow chart showing the basic operation of the CT data processing apparatus according to the present invention.

Next, the operation of the CT data processing apparatus 10 thus configured will be described. As an example, the operation when separating the subcutaneous fat region from visceral fat region of a rat is described. FIG. 4 is a flow chart showing the basic operation of the CT data processing apparatus 10.

The CT data processing apparatus 10 accumulates CT data imaged by the X-ray CT apparatus 5 in the storage part 12 in advance. The CT data processing apparatus 10 first carries out first tomographic data processing using the accumulated CT data (step S1). The first tomographic data processing refers to the first tomographic CT data processing when carrying out three-dimensional analysis. The first tomographic data processing will be described later. Next, continuous tomographic data processing is carried out (step S2). The continuous tomographic data processing refers to the second and later tomographic CT data processing. The continuous tomographic data processing will be described later. Then, whether or not the processing of all the tomographic data for carrying out three-dimensional analysis is completed is determined (step S3). When it is determined that the processing of all the tomographic data is not completed yet, the procedure returns to step S2. When it is determined that the processing of all the tomographic data is completed, the processing is terminated.

Figure 5:
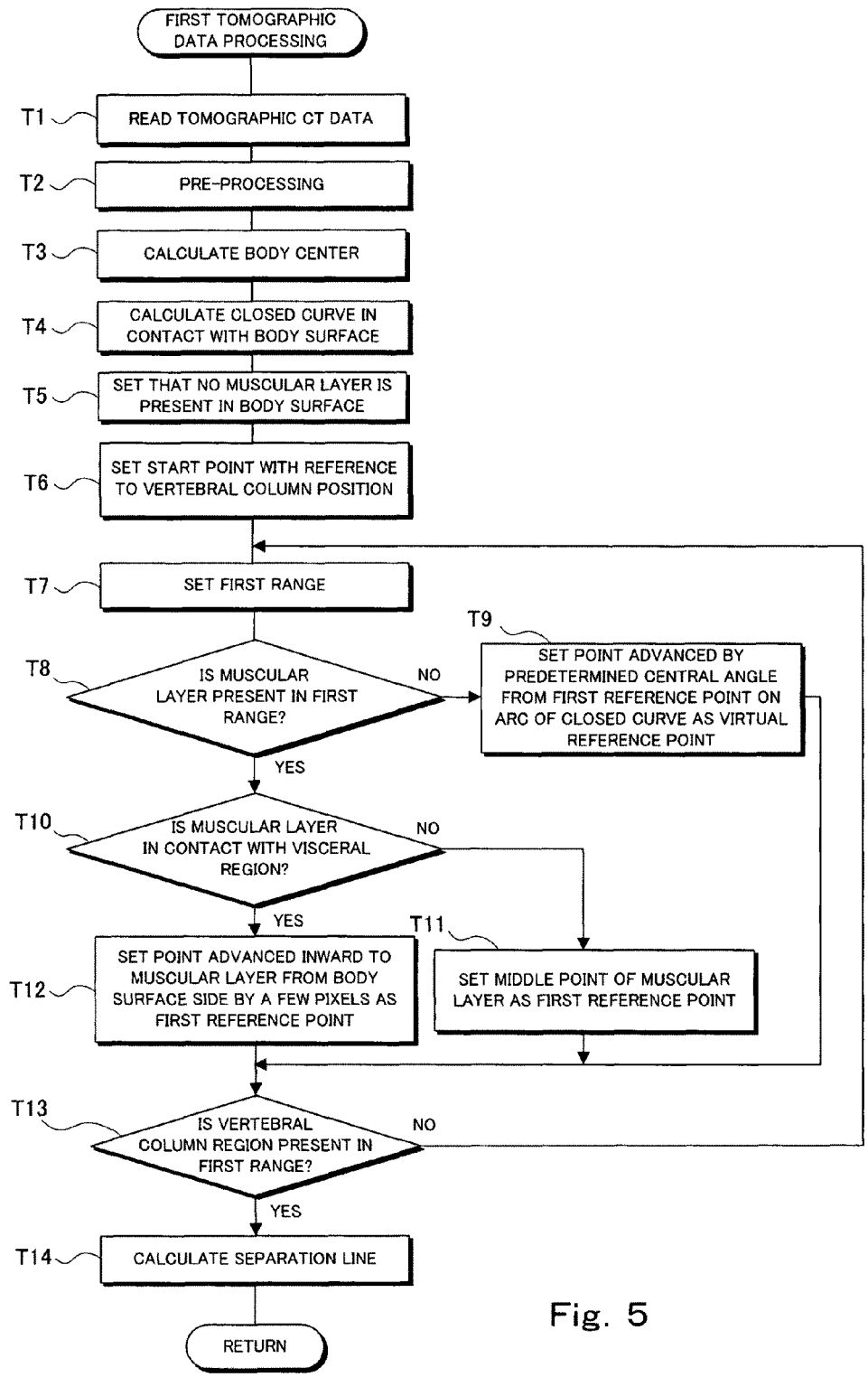
FIG. 5 is a flow chart showing the procedure of first tomographic data processing.

Next, the specific contents of the first tomographic data processing will be described. FIG. 5 is a flow chart showing the procedure of the first tomographic data processing. First, the CT data processing apparatus 10 reads target tomographic CT data from the CT data accumulated in the storage part 12 (step T1). Then, pre-processing is carried out (step T2). The pre-processing refers to processing of changing the data of the portion adjacent to air into the CT value of air or processing of changing the data of the region of the support base into the CT value of air.

Figure 6A:
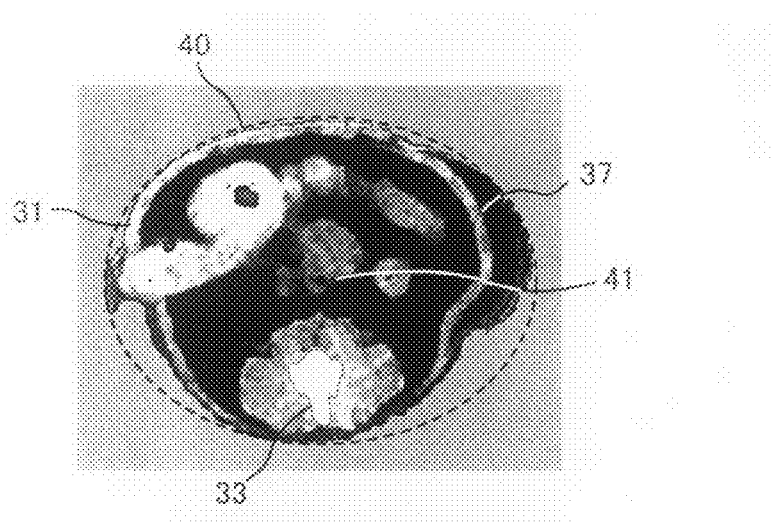
FIGS. 6A to 6C are diagrams showing tomographic CT data step by step along the processing.
Figure 6B:
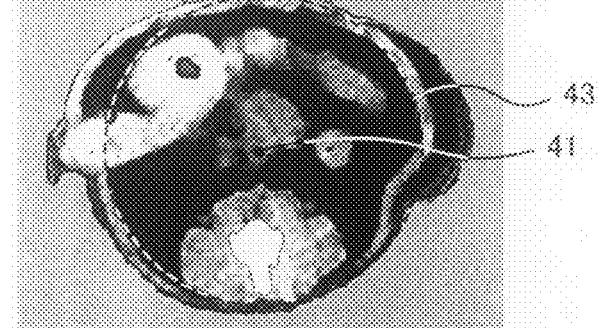
Figure 6C:
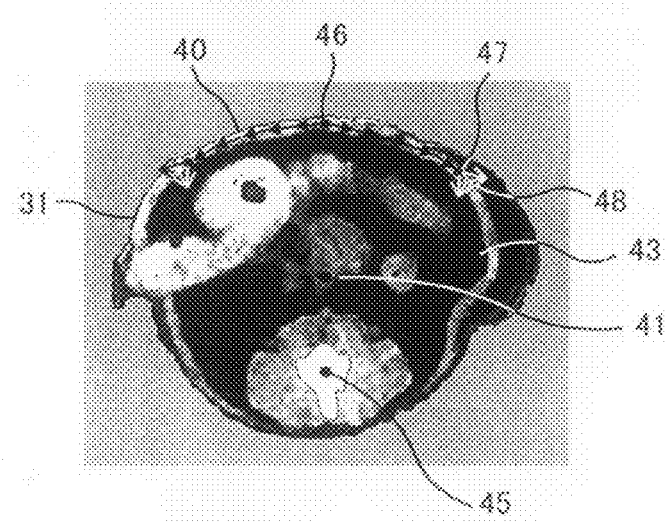

FIGS. 6A to 6C are diagrams showing pre-processed tomographic CT data step by step along the procedure of the processing. In FIGS. 6A to 6C, the processing method until whether or not the muscular layer is present is determined is shown step by step. In FIGS. 6A to 6C, the region of air is shown by a bright color for convenience. For the pre-processed tomographic CT data, the body center is calculated first (step T3). In other words, the body surface region 31 is identified using the CT value and the maximum value and the minimum value of the components of two axes perpendicular to each other in the body surface region 31 are measured. Then, the middle point between the maximum value and the minimum value of each of the axes is extracted as the body center 41.

Next, the closed curve 43 in contact with the body surface region 31 is calculated (step T4). Here, a case where the closed curve 43 is a circle is described. When the closed curve is a circle, the closed curve 43 can be calculated by finding the point closest to the body center 41 in the body surface region 31. Then, it is set so that the muscular layer 37 is not present in the body surface region 31 before the determination processing of the muscular layer (step T5). This setting is carried out by changing the CT value of the body surface region 31 to the CT value of air only during the period of determination processing, for example.

Then, the vertebral column position 45 is identified in the tomographic CT data and the start point 46 is set on the closed curve 43 on the opposite side with respect to the body center 41 by referring to the vertebral column position 45 (step T6). The calculation of the vertebral column position 45 is carried out by identifying the vertebral column region 33 using the CT value and by, for example, finding the center of the vertebral column region 33 as the vertebral column position 45. The start point 46 is identified by finding the intersection of the straight line connecting the vertebral column position 45 and the body center 41 and the boundary of the body surface region 31 and by moving the intersection toward the center by a few pixels. Next, the range 48 (first range) is set (step T7). For example, a point advanced by a central angle of 5 degrees is sought for in the arc direction of a similar curve of the closed curve 43 based on the reference point 47 (first reference point) and a range is determined, which has a fixed width in the radial direction of the body center 41 with the point as center. When the closed curve 43 is a circle, the range 48 is set at the position advanced by the central angle θ on the arc of a circle having a radius r from the body center 41. Then, determination is made by moving the reference point 47. The solid triangular arrow in FIG. 6C shows the direction of movement of the reference point 47 so far and the V-shaped arrow shows the current range 48. This also applies to the subsequent drawings.

Figure 7A:
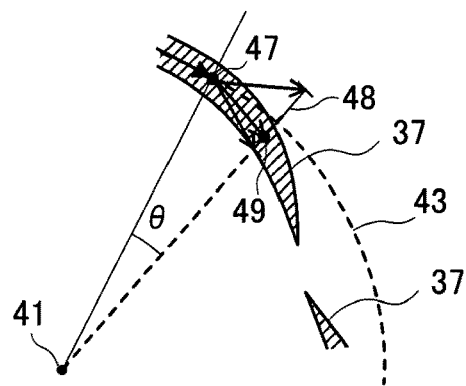
FIG. 7 is a partially enlarged schematic diagram of an image of the tomographic CT data.
Figure 7B:
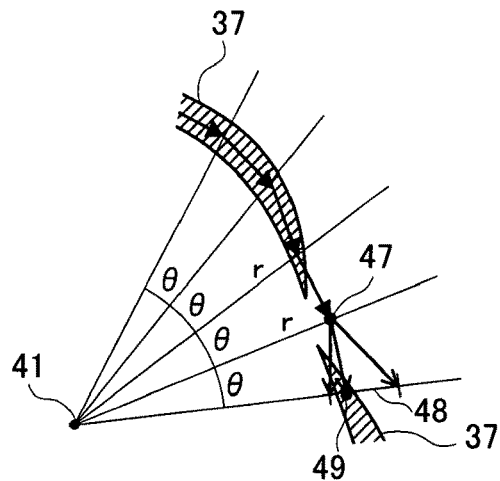
Figure 7C:
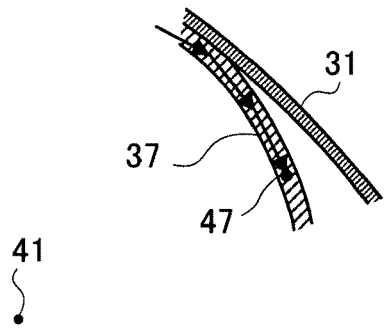

FIGS. 7A to 7C are partially enlarged schematic diagrams of images of the tomographic CT data. The determination processing will be described using these drawings. In the determination processing, whether or not the muscular layer 37 is present in the range 48 is determined first while moving the reference point 47 in a constant direction on the closed curve 43 (step T8). The range 48 (first range) includes a point advanced by the predetermined central angle θ with the body center 41 as center in the arc direction of a similar curve of the closed curve 43 from the reference point 47 and is a range that has its width in the radial direction from the body center 41. As described above, the range 48 is preferably a range with a point advanced by the central angle θ in the arc direction from the reference point 47 as center, however, this point does not necessarily have to be the center. Preferably, the size of the rang is set in advance and it is sufficient if the range is set to the maximum range in which the muscular layer may be present empirically. FIG. 7A schematically shows the case where the muscular layer 37 is found on the side of the body center 41 when the range 48 is searched. As shown in FIG. 7A, when the muscular layer 37 is found, the reference point 47 is set at a middle point 49 of the muscular layer 37 on the line in the radial direction from the body center 41.

When it is determined that the muscular layer 37 is not present in the range 48, the reference point 47 is set virtually at a point advanced by the predetermined central angle θ from the reference point 47 on the arc of a similar curve of the closed curve 43 (step T9). Then, the procedure proceeds to step T13.

The muscular layer 37 is not necessarily present continuously along the circumference and may be partially discontinuous. FIG. 7B schematically shows the case where the reference point 47 passes through the discontinuous portion of the muscular layer 37. As shown in FIG. 7B, when it is determined that the muscular layer 37 is not present in the range 48, the reference point 47 is directly advanced to the next position and the reference point 47 is plotted virtually at the position advanced by the central angle θ on the arc of a circle having radius r from the body center 41. Then, the muscular layer 37 is searched for in the range 48 further advanced by the central angle θ on the arc of a circle having radius r from that position and if the muscular layer 37 is present, the middle point 49 of the muscular layer 37 is set as the reference point 47 after movement.

On the other hand, when it is determined that the muscular layer 37 is present in the range 48, whether or not the muscular layer 37 is in contact with the visceral 38 (parenchymatous organ) is determined (step T10). This determination is made based on the size of the range that has the CT value equivalent to that of the muscular layer 37. In other words, when it is determined that the muscular layer 37 is present, which is remarkably thicker than a general muscular layer, it is determined that the muscular layer 37 is in contact with the visceral 38. When it is determined that the muscular layer 37 is not in contact with the visceral 38 (parenchymatous organ), the middle point of the muscular layer 37 is set as the new reference point 47 (step T11) and the new reference point 47 is stored in the storage part 12. It is preferable to set the middle point as the new reference point 47, however, not limited thereto. When it is determined that the muscular layer 37 is in contact with the visceral (parenchymatous organ) 38, a point moved inwardly to the muscular layer 37 from the side of the body surface region 31 by a few pixels is set to the reference point 47 (step T12). The amount of movement by a few pixels can be determined by, for example, the empirical rules.

There may be the case where the muscular layer 37 is continuous with the body surface region 31 depending on the tomographic CT data as shown in FIG. 7C. The muscular layer and the body surface region have almost the same CT value. In such a case, not only the muscular layer 37 but also the body surface region 31 are found between the reference point 47 and the range 48 and it might be determined that the two muscular layers 37 are present. In order to prevent such an event from occurring, setting is made in advance so that it is determined that the muscular layer 37 is not present in the body surface region 31. Due to this, the determination is not confused even at a portion in which the muscular layer seems to branch.

Next, whether or not the vertebral column region 33 is present in the range 48 is determined when whether or not the muscular layer 37 is present is determined (step T13). When it is determined that the vertebral column region 33 is not present in the range 48, the procedure returns to step T7. On the other hand, when it is determined that the vertebral column region 33 is present in the range 48, a separation line is calculated by linking the points on the muscular layer 37 (step T14) and the procedure is returned. The calculation of the separation line is done by connecting the traces of the reference points 47. In this manner, by calculating the separation line by connecting the traces of the reference points 47, the separation line is calculated by plotting the middle point of the muscular layer 37 on the straight line in the radial direction from the body center 41. The most suitable point for the separation line among those of the muscular layer is the middle point of the muscular layer 37.

In the above processing, the setting is made in advance so that the muscular layer 37 is not present in the body surface region 31, however, if it is determined that the muscular layer is present in the body surface region 31 at the stage of determination, it may also be possible to further make a determination to ignore the result.

Figure 8:
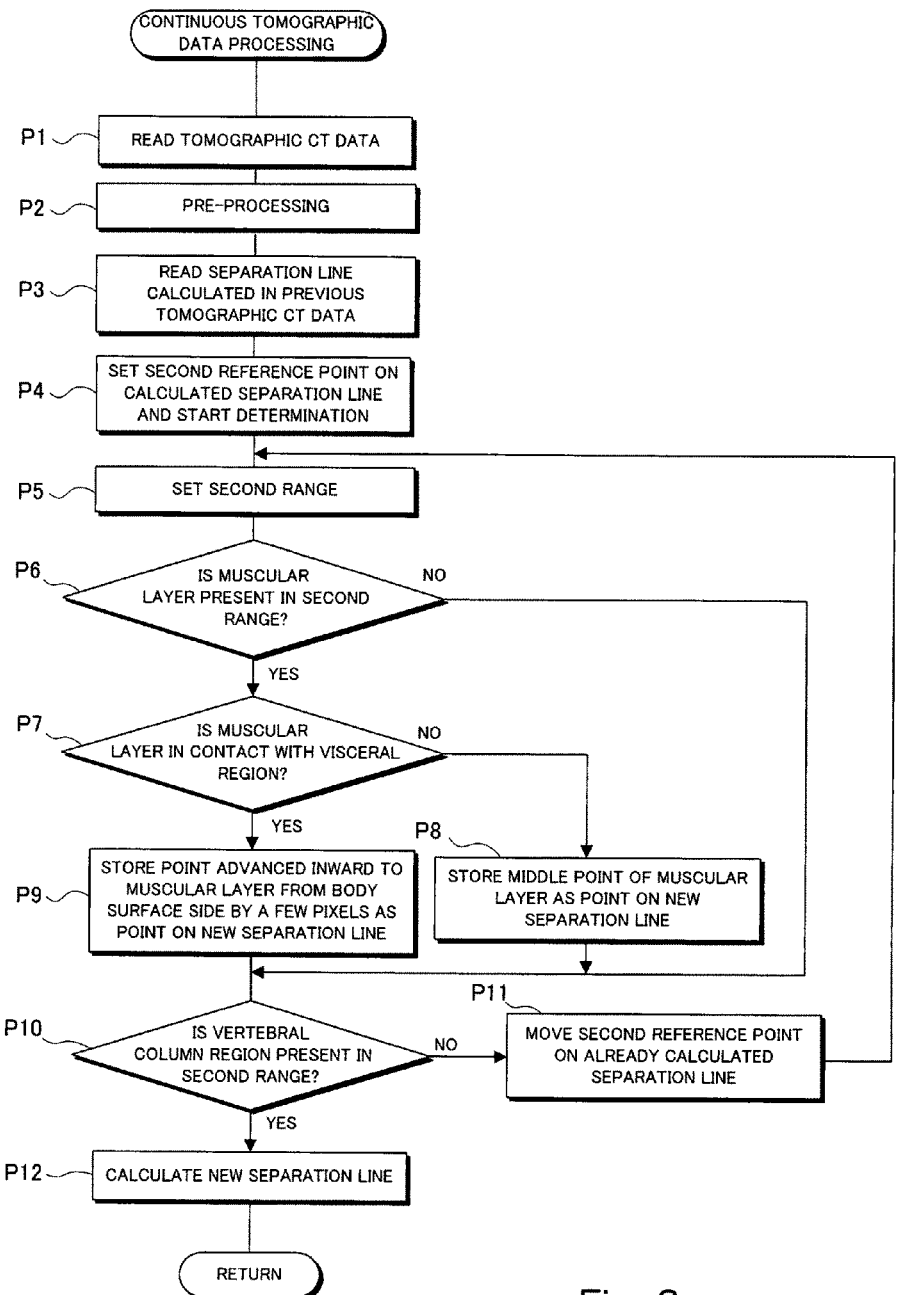
FIG. 8 is a flow chart showing the procedure of continuous tomographic data processing.

Next, the specific contents of the continuous tomographic data processing will be described. FIG. 8 is a flow chart showing the procedure of the continuous tomographic data processing. When this processing is carried out, a separation line has already been calculated for at least one of the tomographic CT data. In the continuous tomographic data processing, tomographic CT data is read newly from the storage part 12 (step P1) and pre-processing is carried out (step P2). It is assumed that the tomographic CT data next to the tomographic CT data for which the separation line has been calculated in the processing of the tomographic CT data preceding by one is read as new data.

In the processing of the tomographic CT data continuously read, the separation line calculated in the processing preceding by one is read (step P3) and the reference point 47a (second reference point) is moved on the same tomographic path as that of the calculated separation line, and then determination is started (step 4). In this case, the start point 46 is determined by utilizing the vertebral column position 45 and the body center 41 of the CT data used in the processing preceding by one as they are.

Next, the range 48a (second range) is set (step P5) and whether or not the muscular layer 37 is present in the range 48a is determined (step P6). The range 48a includes the reference point 47a and is set as a range that has a fixed width in the radial direction from the body center 41. When it is determined that the muscular layer 37 is not present in the range 48a, the procedure proceeds to step P10. On the other hand, when it is determined that the muscular layer 37 is present in the range 48a, whether or not the muscular layer 37 is in contact with the region of the visceral 38 is further determined (step P7). When it is determined that the muscular layer 37 is not in contact with the region of the visceral 38, the middle point of the muscular layer 37 in the range 48a is stored in the storage part 12 as a point on a new separation line. On the other hand, when it is determined that the muscular layer 37 is in contact with the region of visceral 38, a point advanced by a few pixels inward to the center of the muscular layer 37 from the side of the body surface region 31 is stored in the storage part 12 as a point on a new separation line (step P9). In this case also, it is preferable to set the middle point of the muscular layer 37 as a point on a separation line 51, however, the point is not limited necessarily to the center.

Next, whether or not the vertebral column region 33 is present in the range 48a is determined when whether or not the muscular layer 37 is present is determined (step P10). When it is determined that the vertebral column region 33 is not present in the range 48a when whether or not the muscular layer 37 is present is determined, the reference point 47a is moved to the next position on the path 50 of the calculated separation line (step P11) and the procedure returns to step 5. The movement is made by the central angle θ each time with the body center 41 as center. θ is selected to be, for example, 5 degrees. On the other hand, when it is determined that the vertebral column region 33 is present in the range 48a when whether or not the muscular layer 37 is present is determined, the separation line 51 is newly calculated by linking the stored points (step P12) and the procedure is returned.

In the above embodiment, the subcutaneous fat region and the visceral fat region of an examinee such as a rat are finally separated three-dimensionally, however, the result of separation of the fat may be utilized as two-dimensional data on the tomographic CT data obtained respectively.

EXPERIMENTAL EXAMPLE

It was proved that the subcutaneous fat and the visceral fat of a rat can be separated using the above-mentioned CT data processing apparatus 10. First, X-ray CT tomography was carried out using a rat. After an anesthetic injection was given, the rat was laid down on the support base. Then, the support base was inserted into the hole of the gantry of the X-ray CT apparatus 5 and X-ray CT tomography was carried out. As the X-ray CT apparatus 5, R_mCT (3D micro X-ray CT for experimental animal made by Rigaku) was used. Tomograms were taken at intervals of 50 µm and it took about 17 seconds.

Next, the obtained CT data was received by the CT data processing apparatus 10 and processing to separate the fat region was carried out. First, the tomographic region to be measured was specified, the first tomographic CT data at the farthest end was read, and the first tomographic data processing was carried out. Then, the tomographic CT data next thereto was read and the continuous tomographic data processing was carried out sequentially.

FIG. 9 is an image showing the result of the separation processing of the fat region. As shown in FIG. 9, it was possible to separate a subcutaneous fat region 61 from a visceral fat region 62 in the body of the rat by the separation line 51. It can be seen from the images of the three tomographic planes, that is, the plane (axial) perpendicular to the rotation axis of the rotary arm of the X-ray CT apparatus 5 and two planes (sagittal, coronal) parallel to the rotation axis of the rotary arm and perpendicular to each other, that the subcutaneous fat region 61 and the visceral fat region 62 are separated in the tomographic range along the fixed direction of the length of the body.

In the above embodiment, the range 48 is assumed to be a range that has a width in the radial direction from the body center 41, however, it may be a range on an arc at a fixed distance from the reference point 47. In such a case, a range may be set such that it is included in a range of a predetermined angle with the reference point 47 as center, the direction of tangent of the closed curve 43 at the reference point 47 being assumed to be zero degree.

What is claimed is:

1. A CT data processing apparatus comprising:
a center calculation part calculating a body center of an examinee on tomographic CT data;
a start point setting part identifying a vertebral column position on said tomographic CT data and setting a start point at which a first reference point for determination is initially placed on a muscular layer on the opposite side of said vertebral column position with respect to said body center;
a muscular layer determination part determining whether or not a muscular layer is present in a first range set based on said first reference point, and when it is determined that the muscular layer is present in said first range, setting a point on the muscular layer in said first range as a new first reference point and thus determining whether or not the muscular layer is present in said first range while moving said first reference point from said start point; and a separation line calculation part calculating a separation line so that the separation line separating a subcutaneous fat region from a visceral fat region passes through said first reference points.

2. The CT data processing apparatus according to claim 1, wherein
said muscular layer determination part sets said first range in a region advanced from said first reference point in the arc direction of a circle or ellipse with said body center as center and determines whether or not the muscular layer is present.

3. The CT data processing apparatus according to claim 2, wherein
said separation line calculation part calculates a separation line by linking the traces of said first reference points by arcs of circle or ellipse with said body center as center.

4. The CT data processing apparatus according to claim 3, further comprising
a determination condition setting part preliminarily setting a condition for determination that the muscular layer is not present in a body surface region in order to distinguish the body surface region from the muscular layer both having the equivalent CT value prior to said determination.

5. The CT data processing apparatus according to claim 2, further comprising
a determination condition setting part preliminarily setting a condition for determination that the muscular layer is not present in a body surface region in order to distinguish the body surface region from the muscular layer both having the equivalent CT value prior to said determination.

6. The CT data processing apparatus according to claim 1, wherein
said separation line calculation part calculates a separation line by linking the traces of said first reference points by arcs of circle or ellipse with said body center as center.

7. The CT data processing apparatus according to claim 6, further comprising
a determination condition setting part preliminarily setting a condition for determination that the muscular layer is not present in a body surface region in order to distinguish the body surface region from the muscular layer both having the equivalent CT value prior to said determination.

8. The CT data processing apparatus according to claim 1, further comprising
a determination condition setting part preliminarily setting a condition for determination that the muscular layer is not present in a body surface region in order to distinguish the body surface region from the muscular layer both having the equivalent CT value prior to said determination.

9. A CT data processing apparatus comprising:
a muscular layer determination part determining whether or not a muscular layer is present in a second range set based on a second reference point, in tomographic CT data next to tomographic CT data for which a separation line separating a subcutaneous fat region from a visceral fat region of an examinee has already been calculated, while moving said second reference point for determination on a tomographic path identical to said calculated separation line; and a separation line calculation part calculating a separation line so that the separation line passes through a point on the muscular layer in said second range when it is determined that the muscular layer is present in said second range.

10. The CT data processing apparatus according to claim 9, wherein
said separation line calculation part separates the subcutaneous fat region from the visceral fat region three-dimensionally by repeating the calculation of the separation line in each of the second and subsequent tomographic CT data.

11. A CT data processing method causing a computer to execute:
center calculation processing for calculating a body center of an examinee on tomographic CT data;

start point setting processing for identifying a vertebral column position on said tomographic CT data and setting a start point at which a first reference point for determination is initially placed on a muscular layer on the opposite side of said vertebral column position with respect to said body center;

a muscular layer determination processing for determining whether or not a muscular layer is present in a first range set based on said first reference point, and when it is determined that the muscular layer is present in said first range, setting a point on the muscular layer in said first range as a new first reference point and thus determining whether or not the muscular layer is present in said first range while moving said first reference point from said start point; and a separation line calculation processing for calculating a separation line so that the separation line separating a subcutaneous fat region from a visceral fat region passes through said first reference points.

12. A CT data processing method causing a computer to execute:
a muscular layer determination processing for determining whether or not a muscular layer is present in a second range set based on a second reference point, in tomographic CT data next to tomographic CT data for which a separation line separating a subcutaneous fat region from a visceral fat region of an examinee has already been calculated, while moving said second reference point for determination on a tomographic path identical to said calculated separation line; and a separation line calculation processing for calculating a separation line so that the separation line passes through a point on the muscular layer in said second range when it is determined that the muscular layer is present in said second range.

* * * * *